United States Patent
Dewa et al.

(10) Patent No.: US 8,830,581 B2
(45) Date of Patent: Sep. 9, 2014

(54) BROADBAND POLARIZATION SWITCHING

(75) Inventors: Paul G Dewa, Newark, NY (US);
Michael M Dunn, Palmtya, NY (US);
Stephen K Mack, Rush, NY (US);
Brian Monroe McMaster, Pittsford, NY (US); Robert L Michaels, Rochester, NY (US); Paul Francis Michaloski, Rochester, NY (US)

(73) Assignee: Corning Incorporated, Corning, NY (US)

( * ) Notice: Subject to any disclaimer, the term of this patent is extended or adjusted under 35 U.S.C. 154(b) by 125 days.

(21) Appl. No.: 13/461,879

(22) Filed: May 2, 2012

(65) Prior Publication Data
US 2013/0070331 A1    Mar. 21, 2013

Related U.S. Application Data

(60) Provisional application No. 61/536,686, filed on Sep. 20, 2011.

(51) Int. Cl.
| | |
|---|---|
| G02B 27/28 | (2006.01) |
| G02B 5/30 | (2006.01) |
| G01N 21/33 | (2006.01) |
| G01N 21/21 | (2006.01) |
| G02B 6/27 | (2006.01) |

(52) U.S. Cl.
CPC ............ *G02B 27/286* (2013.01); *G02B 5/3083* (2013.01); *G01N 21/33* (2013.01); *G02B 27/283* (2013.01); *G01N 21/21* (2013.01); *G02B 6/2773* (2013.01)
USPC ........................ 359/489.09; 359/352; 359/320

(58) Field of Classification Search
CPC ............. G02F 1/31; G02F 1/093; G02B 1/02; G02B 5/3083; G02B 6/272; G02B 6/2766; G02B 6/29302; G02B 6/35; G02B 6/3528; G02B 13/10; G02B 27/283; G02B 27/28; G02B 27/286; H04Q 11/005; H04Q 2011/0035; H04Q 2011/0024; G01J 3/0232
USPC .............. 359/489.09, 487.04, 489.1, 484.04, 359/489.15, 320, 489.05, 223.1, 489.01, 359/350–362, 368, 379–386, 388, 838, 850, 359/862–863, 865, 871–878, 881, 359/196.1–226.2, 618, 629, 634, 636, 638, 359/839; 385/36
See application file for complete search history.

(56) References Cited

U.S. PATENT DOCUMENTS 4,059,343 A * 11/1977 Kowalski et al. ............. 359/669
4,187,803 A    2/1980 Valenta ............................. 119/1
(Continued)

FOREIGN PATENT DOCUMENTS

| EP | 653660 A1 * | 5/1995 | .............. G02F 1/09 |
|---|---|---|---|
| EP | 1780530 | 5/2007 | |
| GB | 885261 | 12/1961 | |

OTHER PUBLICATIONS

CVI Melles Griot: "Rochon Prism Polarizers" http://www.cvimellesgriot.com/products/documents/catalog/RCHP.pdf.

(Continued)

*Primary Examiner* — Thomas K Pham
*Assistant Examiner* — Nicholas Pasko
(74) *Attorney, Agent, or Firm* — Svetlana Short

(57) ABSTRACT

A polarization switching apparatus has a first birefringent polarizer formed as a composite prism and disposed to direct incident light of a first polarization along a first optical path and light of a second polarization along a second optical path, wherein the second optical path is oblique to the first optical path. A beam redirector is disposed to redirect the first optical path from the first birefringent polarizer toward an input face of a second birefringent polarizer; wherein the second birefringent polarizer is also formed as a composite prism and is disposed to combine incident light of the first and second polarizations onto a common output path. A shutter apparatus is actuable to selectively block light of the first polarization or light of the second polarization from the input face of the second birefringent polarizer.

20 Claims, 13 Drawing Sheets

(56) References Cited

U.S. PATENT DOCUMENTS

| | | | |
|---|---|---|---|
| 5,276,747 A | 1/1994 | Pan | 385/34 |
| 5,877,859 A * | 3/1999 | Aspnes et al. | 356/364 |
| 5,945,037 A * | 8/1999 | Ebbers | 252/585 |
| 6,124,928 A * | 9/2000 | Slater | 356/317 |
| 6,285,500 B1 * | 9/2001 | Ranalli et al. | 359/245 |
| 6,535,311 B1 * | 3/2003 | Lindquist | 398/82 |
| 7,054,051 B1 * | 5/2006 | Bloom | 359/276 |
| 7,599,069 B2 * | 10/2009 | Toussaint et al. | 356/491 |
| 2003/0053209 A1 * | 3/2003 | Chang et al. | 359/484 |
| 2003/0152316 A1 * | 8/2003 | Zhou | 385/20 |
| 2004/0090601 A1 | 5/2004 | Nakanishi et al. | |
| 2005/0036202 A1 * | 2/2005 | Cohen et al. | 359/495 |
| 2006/0114542 A1 | 6/2006 | Bloom | 359/276 |
| 2007/0109551 A1 | 5/2007 | Aiyer | |

OTHER PUBLICATIONS

PCT/US2012/054089 Search Report.

* cited by examiner

BROADBAND POLARIZATION SWITCHING

CROSS REFERENCE TO RELATED APPLICATIONS

This application claims the benefit of U.S. Provisional Patent Application Ser. No. 61/536,686, filed on Sep. 20, 2011, entitled "BROADBAND POLARIZATION SWITCHING" in the names of Paul Dewa et al., the contents of which are incorporated fully herein by reference.

FIELD OF THE INVENTION

This invention generally relates to optical apparatus for selecting polarized light in an optical system and more particularly relates to a broadband polarization switching apparatus capable of switching polarized light over a broad wavelength range that includes light in the deep ultraviolet range.

BACKGROUND

In high performance optical metrology and inspection systems, such as those used for semiconductor wafer inspection, the industry trend is to inspect a sample using multiple optical configurations in a serial fashion. The configuration options may include wavelength, illumination partial coherence (illumination sigma), and polarization state. In order to have high throughput, the optical configurations of the inspection system must be switched from one to the next in a very short time while imparting negligible levels of shock and vibration to the inspection system.

Although there are a number of types of polarizers, many types of polarizers are constrained to particular spectral bands and perform poorly with light outside the intended band. Thin-film polarizers, for example, are typically designed for narrow spectral bands, centered about a nominal wavelength. Wire grid polarizers work best primarily for handling light in the infrared region. Electro-optic and acousto-optic devices have limited spectral bandwidth and power ranges. The use of half-wave retarding plates in conjunction with static polarizers is not practical for broadband light and will not work for the full range of light that extends from deep ultraviolet (DUV, such as around 200 nm) to infrared (IR, such as around 800 nm). Still other polarizer types may work well in specific spectral regions and very poorly in others.

For performance over a broad range of wavelengths that include the DUV region, the selection is more limited. Polarizers that operate in this range and that meet the requirements for broad range operation are generally composite devices that use paired arrangements of birefringent crystals, coupled together along an interface and disposed at an appropriate position and angle in the light path for polarizing the incident light. Devices of this type, however, are typically large in volume and in mass. This makes it difficult to switch the polarization state quickly and without imparting some amount of shock and vibration to the inspection system.

Thus, although various types of polarization switching apparatus are used in narrow-band applications, these solutions are not suitable for broadband application, particularly where the spectral range spans the DUV wavelengths. There is, then, a need for a broadband polarization switching apparatus that is capable of handling light in the DUV region, but without requiring rotation of the polarizer itself as part of the switching operation.

SUMMARY

To advance the art of polarization switching, such as is needed for optical metrology and inspection systems, embodiments of the present invention use an arrangement of polarizers and shutter devices that allow the handling of broadband light and allow the use of either of two orthogonal polarization states or, optionally, of all polarization states. Advantageously, embodiments of the present invention allow switching of polarization states at high speeds without the need to rotate the polarizers themselves.

According to an aspect of the present invention, there is provided a polarization switching apparatus comprising:
   a first birefringent polarizer formed as a composite prism and disposed to direct incident light of a first polarization along a first optical path and light of a second polarization along a second optical path, wherein the second optical path is oblique with respect to the first optical path;
   a beam redirector disposed to redirect the first optical path from the first birefringent polarizer toward an input face of a second birefringent polarizer; wherein the second birefringent polarizer is also formed as a composite prism and is disposed to combine incident light of the first and second polarizations onto a common output path; and
   a shutter apparatus that is actuable to selectively block light of the first polarization or light of the second polarization from the input face of the second birefringent polarizer.

From another aspect, the present invention provides a polarization switching apparatus comprising:
   a first birefringent polarizer and a second birefringent polarizer, each formed as a composite prism with an input face and an output face, and both disposed on an optical axis, wherein the second birefringent polarizer has a reversed orientation from the first birefringent polarizer;
   a beam redirector disposed to redirect light of a first polarization from the output face of the first birefringent polarizer toward the input face of the second birefringent polarizer; and
   a shutter apparatus actuable to selectively block either light along the optical axis between the first and second birefringent polarizers or the light of the first polarization.

Other desirable objectives, features, and advantages of the disclosed invention may occur or become apparent to those skilled in the art. The invention is defined by the appended claims.

DETAILED DESCRIPTION

Figure 1B:
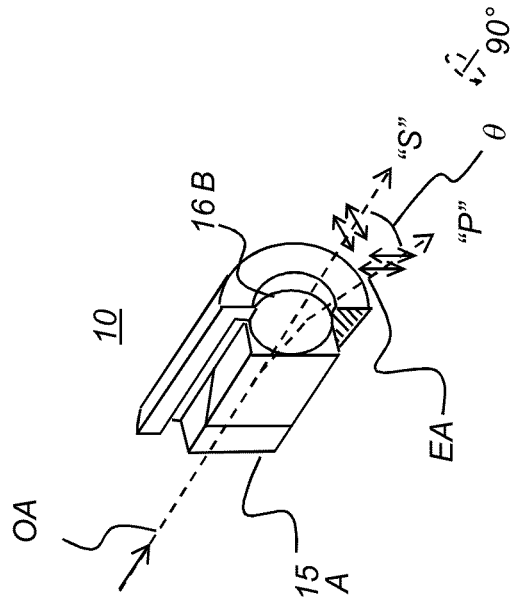
FIG. 1B is a perspective view that shows a Rochon polarizer separating light of first and second polarizations, with the polarizer rotated to a second rotational orientation.

Figures shown and described herein are provided in order to illustrate key principles of operation and fabrication for an optical apparatus according to various embodiments and a number of these figures are not drawn with intent to show actual size or scale. Some exaggeration may be necessary in order to emphasize basic structural relationships or principles of operation.

Where they are used in the present disclosure, the terms "first", "second", and so on, do not necessarily denote any ordinal or priority relation, but are used for more clearly distinguishing one element from another. There are no fixed "first" or "second" elements in what is taught herein; these descriptors are merely used to clearly distinguish one element from another similar element in the context of the present disclosure, such as in the order in which like parts are referenced. The term "actuable" has its conventional meaning, relating to a device or component that is capable of effecting an action in response to a stimulus, such as in response to an electrical signal, for example.

In the context of the present disclosure, the term "oblique" means at an angle that is not an integer multiple of 90 degrees. Two beams, for example, are considered to be oblique with respect to each other if they diverge from or converge toward each other at an angle that is at least about 2 degrees or more away from parallel, or at least about 2 degrees or more away from orthogonal.

The term "prism" or "prism element" is used herein as it is understood in optics, to refer to a transparent optical element that is generally in the form of an n-sided polyhedron with flat surfaces upon which light is incident and that is formed from a transparent, solid material that refracts light. It is understood that, in terms of shape and surface outline, the optical understanding of what constitutes a prism is less restrictive than the formal geometric definition of a prism and encompasses that more formal definition. In optics, for example, the term "prism" is also used in reference to a composite element, formed from two or more component prism elements that are glued or otherwise coupled together, including composite elements that are mechanically coupled but have an air gap at the interface between them.

In the context of the present disclosure, the term "broadband" is used to denote a spectral range that at least exceeds about 50 nm. Embodiments of the present invention are not only able to provide polarization switching over a broadband range, but can provide this switching for wavelengths that extend into the deep ultraviolet (DUV) region, for switching light provided by excimer lasers, for example, that emit light below 200 nm. This range, inaccessible to many types of conventional polarizers, can be handled by a birefringent polarizer formed as a sectioned or composite birefringent prism, that is, formed by coupling blocks or wedges of birefringent crystal material.

There are a number of types of composite birefringent prisms. One composite prism of this type is the Rochon polarizer, formed from two birefringent crystal wedges, each wedge termed a component crystal or component prism in the present disclosure. The pair of component crystals are typically cemented together or are otherwise maintained in optical contact at an interface. Alternately, the birefringent component crystals can be coupled to a frame or other holder that maintains a precise, narrow air spacing between them. Typically formed from crystalline materials such as quartz, $MgF_2$, $YVO_4$, alpha-BBO (barium borate), rutile ($TiO_2$), sodium nitrate, or tourmaline, the Rochon polarizer advantageously exhibits a high extinction ratio and has a high damage threshold.

For any of the various types of composite birefringent prisms, the behavior of the prism with respect to incident polarized light depends, in large part, on the optic axis of the crystal material itself. Light that is polarized in parallel to the optic axis of the crystal may be separated from and diverge from light that is polarized perpendicular to the optic axis. This complicates the task of describing the relative polarization states of incident and output light, since, in addition to its position, the orientation and rotation of the composite birefringent prism with respect to the optical system can determine how polarized light behaves. This can be a particular source of confusion in describing an optical system, since the "optic axis" of a crystal may be orthogonal to, or at some other non-zero angle to, what is considered the optical axis for the system itself. For this reason, unless otherwise specified, references in the present disclosure to "optical axis" do not refer to the optic axis of a composite birefringent prism or of its component crystals, but instead refer to the optical axis of the overall polarization switching system that includes the birefringent prisms and other components, as described in detail subsequently.

Figure 1A:
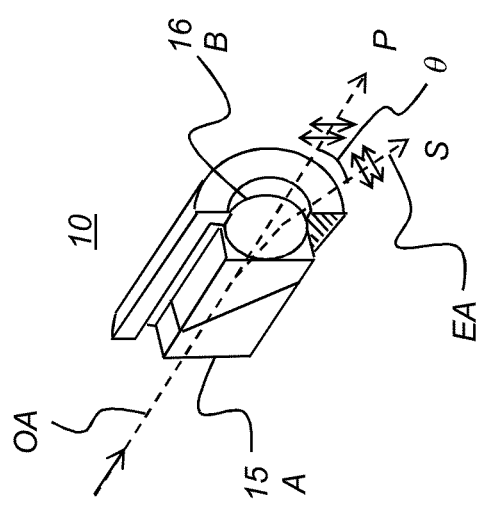
FIG. 1A is a perspective view that shows a Rochon polarizer separating light of first and second polarizations in a first rotational orientation.

FIG. 1A is a perspective view that shows a Rochon polarizer 10 separating light of first and second polarizations. In the orientation shown, polarizer 10 lies along the optical axis OA and provides light of a first polarization state, shown as P-polarized light, parallel to the page, output along axis OA as an ordinary beam. Light of a second polarization state, orthogonal to the P-polarized light and shown as S-polarized light, is redirected as an extraordinary beam, at an angle θ, to axis OA. In conventional use, Rochon polarizer 10 can be rotated ¼ turn (90 degrees) about the OA to switch the polarization state of light along axis OA, as shown in FIG. 1B. In FIG. 1B, the "P" and "S" designations are given to describe polarization states with reference to the assignments shown in FIG. 1A. As can be seen from FIGS. 1A and 1B, rotation of the Rochon polarizer 10 about optical axis OA determines the polarization state of light that exits on that axis. Angle θ between extraordinary axis EA and optical axis OA is oblique, diverging at least about 2 degrees from parallel. The direction of the deviation for this axis follows the orientation of the wedge interface between the component crystals.

Using the principle shown in FIGS. 1A and 1B, a simple polarization switcher can be formed using a single Rochon polarizer 10. A polarization switcher of this type simply rotates polarizer 10 to either of two rotational positions about the optical axis in order to switch between first and second mutually orthogonal polarization states. This can provide a broadband switching polarizer, but there are drawbacks with this switching technique. Significantly, the relative size and mass of the Rochon polarizer constrains the switching speed. In addition, actuator vibration and shock and mechanical tolerances for precision positioning also limit the feasibility of this approach. Thus, a polarization switcher using a rotatable Rochon polarizer would not serve well in an inspection or measurement environment where high-speed switching is needed.

The specific behavior of the Rochon polarizer and similar types of birefringent composite polarizers depends on the arrangement of their component wedges, the angle of the interface between the components, the crystalline material used, and the optic axes of the crystal components. As shown in FIGS. 1A and 1B, the birefringent prism that forms the Rochon polarizer has an input or A-face 15 and an output or B-face 16. Input and output face designations are arbitrary, since these polarizers, when used singly, can be used in either direction. However, it is important to note that, due to interface angle between component prisms and geometry, prism 10 behavior is slightly different depending on whether the A-face 15 or the B-face 16 serves as the input face in the path of incident light. Embodiments of the present invention used matched pairs of Rochon or other birefringent composite prisms, with the two paired prisms disposed in opposite orientation, that is, with one polarizer in reversed orientation from the other, so that the input face/output face or A/B face designations of the two prisms in the pair are the reverse of each other.

Figure 1C:
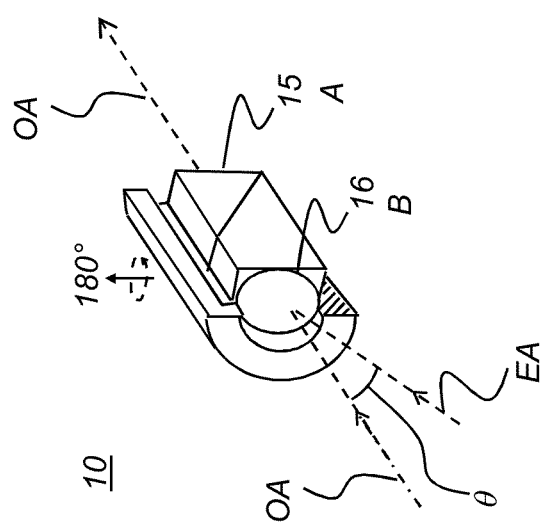
FIG. 1C is a perspective view that shows a Rochon polarizer combining light of first and second polarizations, incident at different angles, onto the optical axis.

FIG. 1C shows Rochon polarizer 10 with a reversed orientation, with respect to incident light, compared with FIGS. 1A and 1B orientations. Rochon polarizer 10 in FIG. 1C is disposed to receive, at what is designated its B-face 16, polarized light of different polarization states, with light of one polarization state at incident angle θ, and to direct light of either polarization state onto optical axis OA at its A-face 15. Again, these input A-/output B-face designations used herein are arbitrarily assigned, but are the same for two paired composite birefringent prisms of the same type and must be identified in order to dispose each prism in its proper orientation for polarization switching in embodiments of the present invention.

Embodiments of the present invention provide a polarization switching apparatus that takes advantage of the broadband performance of Rochon and similar birefringent polarizers formed from crystalline materials and provides improved switching speed by eliminating the requirement for a motor or other actuator to spin the polarizer about the optical axis. In addition, embodiments of the present invention provide polarization switching that allows up to three output states, so that the output light can alternately be of a first polarization only, or of a second polarization only, or of both polarizations, or a suitable combination of these states. Beam redirection optics compensate for differences in refraction due to wavelength, so that the output beam does not deviate in spatial position when switched from one polarization state to the other.

Figure 2A:
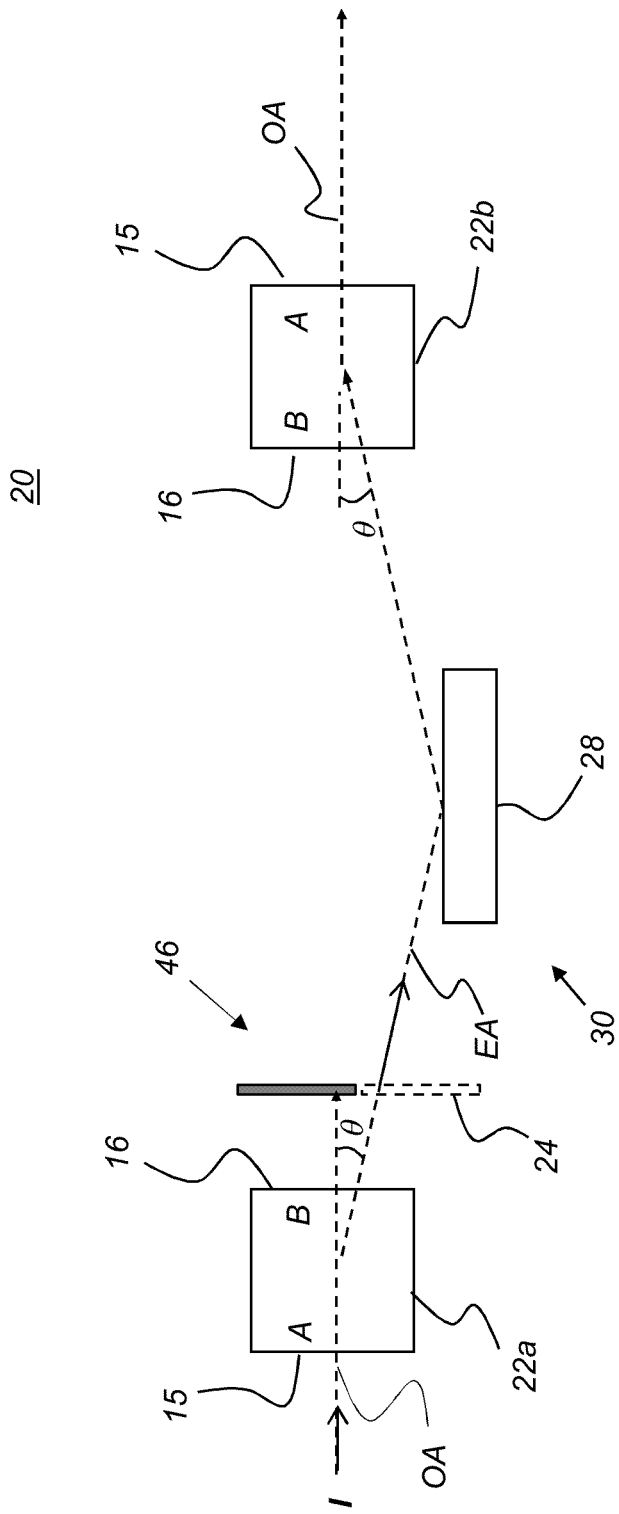
FIG. 2A is a schematic block diagram that shows a broadband polarization switching apparatus using a pair of polarizers and a reflective surface, with a shutter element to block light of an undeviated first polarization state, allowing transmission of the orthogonal polarization state.
Figure 2B:
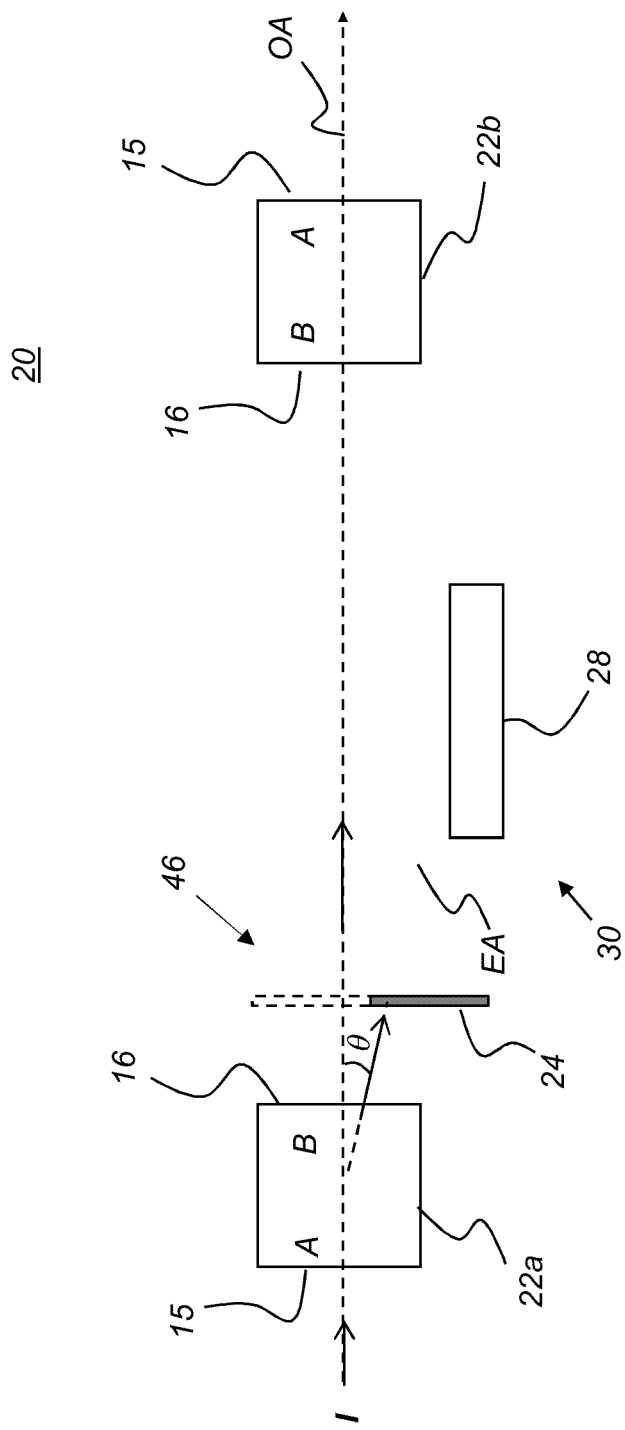
FIG. 2B is a schematic block diagram that shows the use of a shutter element to block light of a deviated second polarization state, allowing transmission of the orthogonal first polarization state.

The schematic diagram of FIGS. 2A and 2B show a polarization switching apparatus 20 consistent with an embodiment of the present invention. Switching apparatus 20 has a first or input polarizer 22a and a second or output polarizer 22b, both aligned along optical axis OA and in reversed orientation with respect to each other. Input polarizer 22a separates the incident light I according to its polarization axis. Light of a first polarization state continues undeviated along the optical axis OA. Light of a second orthogonal polarization state is redirected by redirecting optics 30 along an extraordinary axis EA toward a reflective element 28, such as a mirror. Reflection at a low or "grazing" angle is advantaged for preserving the polarization state of the incident light. As part of a shutter apparatus 46, a shutter element 24 is arranged in the path of the output light from polarizer 22a to block or allow light of either polarization state. In one position, as in FIG. 2A, shutter element 24 blocks the light that would otherwise travel along the path of optical axis OA. In FIG. 2B, the position of shutter element 24 blocks the light along the path of extraordinary axis EA.

In FIGS. 2A and 2B, second or output polarizer 22b, reversed in orientation from polarizer 22a and acting as described in FIG. 1C, combines the reflected EA light path with the undeviated OA path to provide output light of either polarization state, as switched according to shutter element 24, along the optical axis OA. Second polarizer 22b is reversed in A/B orientation relative to first polarizer 22a and functions in reverse, so that light of the orthogonal polarization that is incident along extraordinary axis EA is output along optical axis OA. With this configuration, polarizers 22a and 22b are stationary.

Shutter apparatus 46 can have one or more shutter elements 24 for alternately blocking light of the first or second polarization, depending on the configuration. A single shutter element 24 can also have positions for blocking all of the light, or none of the light, along the light paths between polarizers 22a and 22b. The use of a single shutter element 24, as shown in the examples of FIGS. 2A and 2B, is advantaged for reducing the number of components needed as part of shutter apparatus 46 and allows for the use of a smaller shutter element 24, disposed in proximity to either polarizer 22a or 22b. In an alternate embodiment of the present invention, a pair of shutter elements 24 are used for shutter apparatus 46, actuable in a synchronized manner so that one of the pair of shutter elements 24 is on, blocking one light path, while the other shutter element 24 in the pair is off. In yet another alternate embodiment of the present invention, paired shutter elements 24 are independently actuable to allow light along both, either, or neither light paths.

Shutter element 24 can be a lightweight shutter device for blocking or deflecting light, and can be actuated using a galvanometer or other lightweight actuator that has sufficient speed for the needed switching. Low power is also an advantage with a galvanometric actuator. Consistent with an embodiment of the present invention, shutter element 24 has three effective positions: blocking the internal OA path in a first position as in FIG. 2A; blocking the internal EA path in a second position as in FIG. 2B; or blocking neither path in a third position, thus allowing both polarizations at the output of polarization switching apparatus 20 in this third position. An alternate fourth position allows shutter element 24 to block all of the light. Shutter apparatus 46 can have any suitable control logic arrangement for actuating one or more shutter elements 24 from one state to another, using techniques well known in the optical device arts. In the redirecting optics 30 configuration shown in FIGS. 2A and 2B, reflective element 28 can be a mirror or reflective dichroic or other surface disposed in the path of extraordinary axis EA or, alternately, in the path of optical axis OA.

Figure 3:
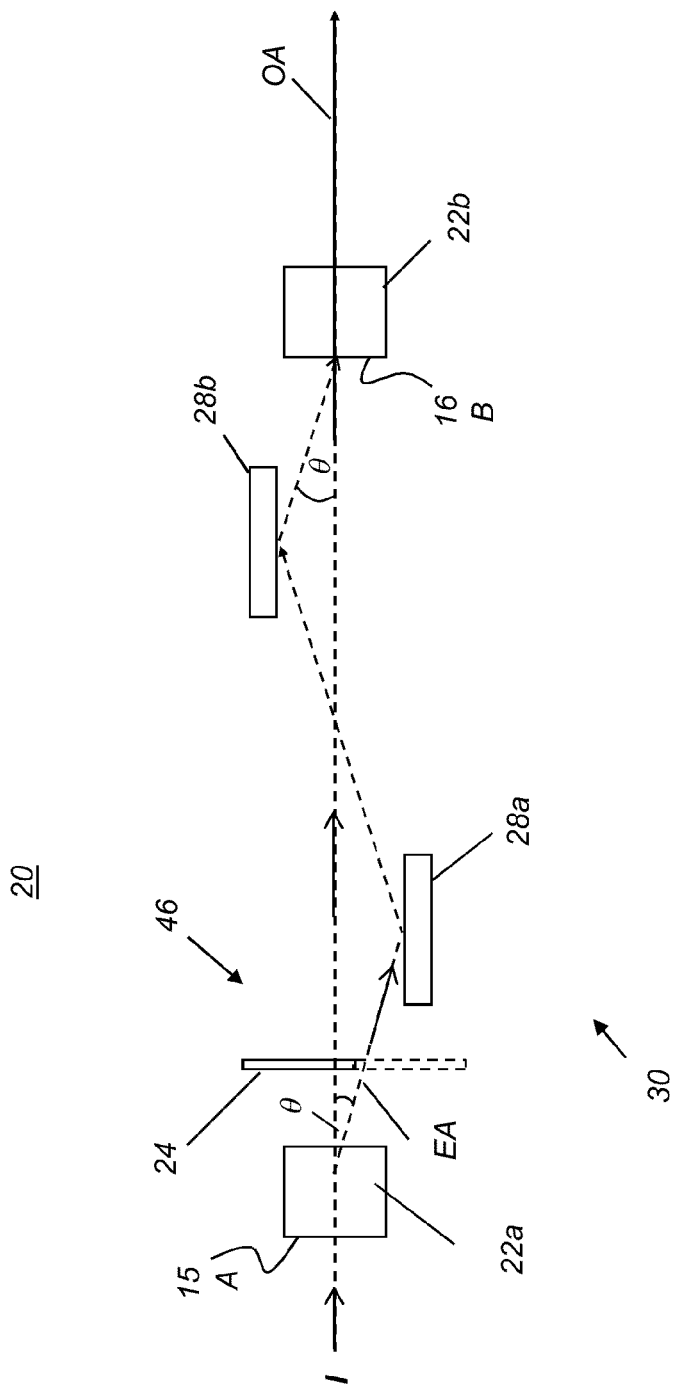
FIG. 3 is a schematic block diagram that shows a broadband polarization switching apparatus using a pair of polarizers and a pair of reflective surfaces.

In the alternate embodiment shown in FIG. 3, redirecting optics 30 includes two reflective elements 28a and 28b, two mirrors or other reflectors, such as dichroic reflectors, for example, that are arranged to revert the image of the redirected beam. Redirecting optics 30 can be any of a number of types of reflective elements, such as mirrors or coated surfaces, as well as refractive elements, such as prisms and lenses.

The Rochon polarizer 10 is achromatic for light of the polarization state that is directed along optical axis OA. For light having the orthogonal polarization state, refraction varies by wavelength. Thus, angle θ in FIGS. 1A, 1B and 2A, 2B, for example, is wavelength-dependent. Angle θ is generally larger for light of shorter wavelengths.

Figure 4A:
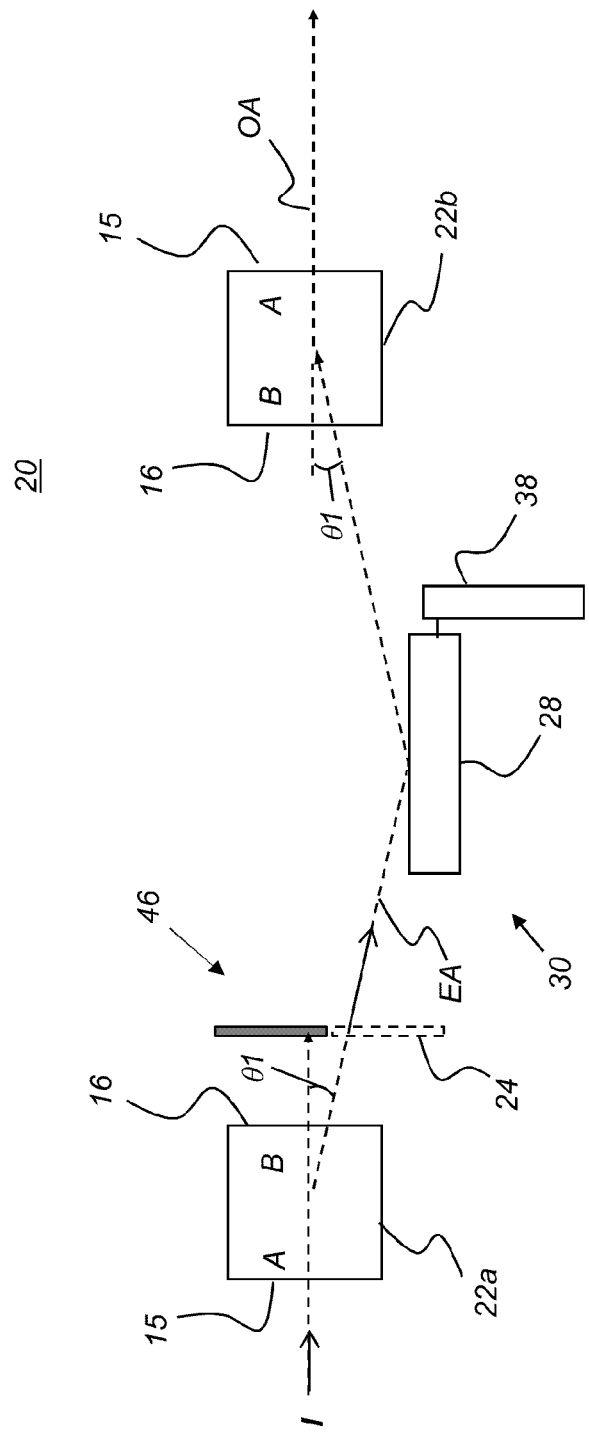
FIGS. 4A and 4B show an adjustment of beam redirector position according to wavelength.
Figure 4B:
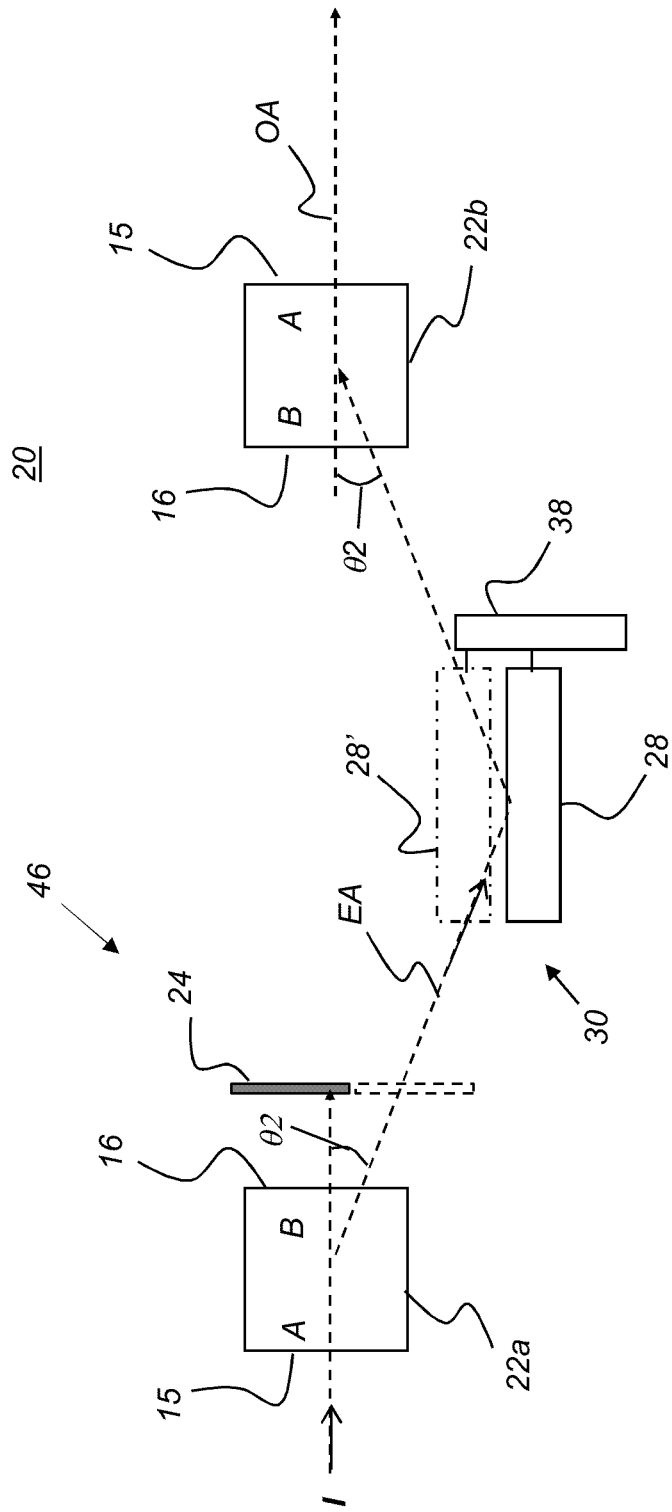

FIGS. 4A and 4B show an embodiment of polarization switching apparatus 20 that adapts for differences in wavelength. In FIG. 4A, with incident light I at a first wavelength, the extraordinary axis EA diverges from the optical axis OA at an angle θ1. An actuator 38 positions reflective element 28 so that light at this angle is redirected at the proper angle toward polarizer 22b. FIG. 4B shows reflective element 28 moved to a different position for redirecting light at a shorter wavelength, where the extraordinary axis EA diverges from the optical axis OA at a larger angle θ2. For reference, the earlier position of reflective element 28 is shown in phantom lines at 28'.

Figure 5A:
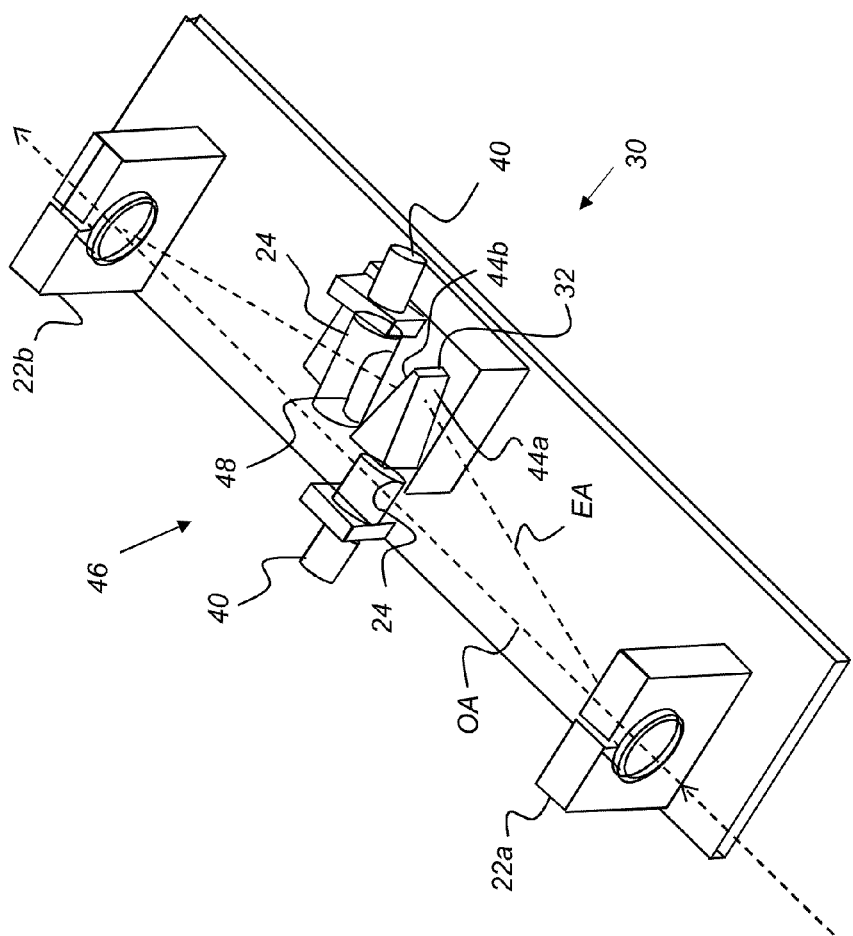
FIG. 5A is a perspective view that shows a broadband polarization switching apparatus using a redirecting prism in the path of the deviated polarization state.
Figure 5B:
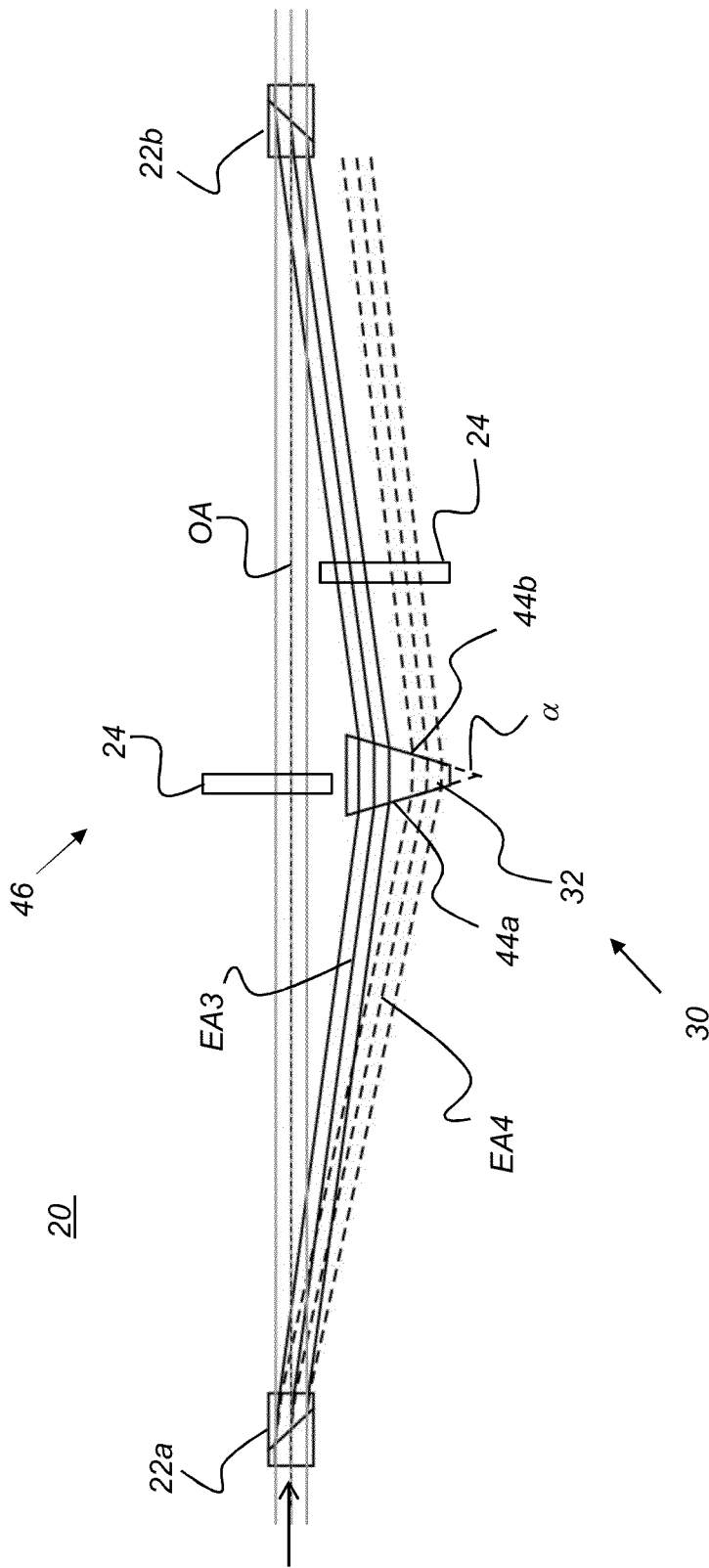
FIG. 5B is a schematic diagram for the apparatus shown in FIG. 5A.

The perspective view of FIG. 5A and schematic diagram of FIG. 5B show an alternate embodiment of the present invention in which redirecting optics 30 uses a refractive element, with a refracting prism 32 to redirect light of the second polarization state back toward the second polarizer 22b. Shutter apparatus 46 is a mechanism having two motors as actuators 40, with each motor used to rotate an actuated shutter element 24 into position, either obstructing the light path or providing an aperture for the light. In the embodiment shown in FIGS. 5A and 5B, shutter apparatus 46 thus has two shutter elements 24 that cooperate to block alternate light paths appropriately.

One difficulty with the single-prism arrangement of FIG. 5A relates to the wavelength of light incident to prism 32 and to its angle of minimum deviation $\delta_m$, which changes according to the wavelength of the incident light. Briefly, when a beam refracts through prism 32 at the angle of minimum deviation, the angle of incidence on a first or incidence face 44a of prism 32 is equal to the angle of exitance of the beam at a second or exit face 44b of prism 32. When incidence and exitance angles are equal, the beam subtends the same size on both faces, without magnification or demagnification of the beam by the prism in the refracting direction. In some applications, magnification of the beam may not be a consideration; however, in precision measurement applications, changes in beam size at different wavelengths can be highly undesirable.

The schematic side view of FIG. 5B shows what happens when conditions for the angle of minimum deviation $\delta_m$ are satisfied for one wavelength and not satisfied for another. Light at one wavelength, shown in solid lines along extraordinary axis EA3, is at the angle of minimum deviation relative to prism 32 and is redirected from polarizer 22a to polarizer 22b. Light at another wavelength is shown in dashed lines along extraordinary axis EA4. This light misses second polarizer 22b altogether.

When arranged to provide minimum deviation, prism 32 is equidistant from polarizers 22a and 22b. The angle of minimum deviation is twice the deviation angle θ from the first polarizer 22a. Prism 32 has a prism angle α, also termed a prism apex angle, and shown by dashed lines in FIG. 5B.

For a prism angle α, the relationship between the refractive index of the prism (n) and the angle of minimal deviation $\delta_m$ is given by:

$$n = \frac{\text{Sin}[(\alpha + \delta_m)/2]}{\text{Sin}[\alpha/2]}$$

The index n of the refractive material of prism 32 is one function of wavelength, and the deviation angle θ of the second polarization at the first polarizer 22a is another function of wavelength. After taking into account both of these functions, it is possible to derive an equation of the optimum prism angle α, as a function of wavelength, to meet the requirement for minimum deviation. In the case of FIGS. 5A and 5B however, with a single prism formed with a set angle α, minimum deviation is satisfied only at one wavelength. It is possible to align the beam to the second polarizer outside of minimum deviation by rotating and translating prism 32, but the beam changes width in the refracting direction when this happens and will no longer match the width of the beam of the first polarization. Thus, even where prism 32 can be rotated or repositioned, some change in beam magnification results at other wavelengths.

Figure 6A:
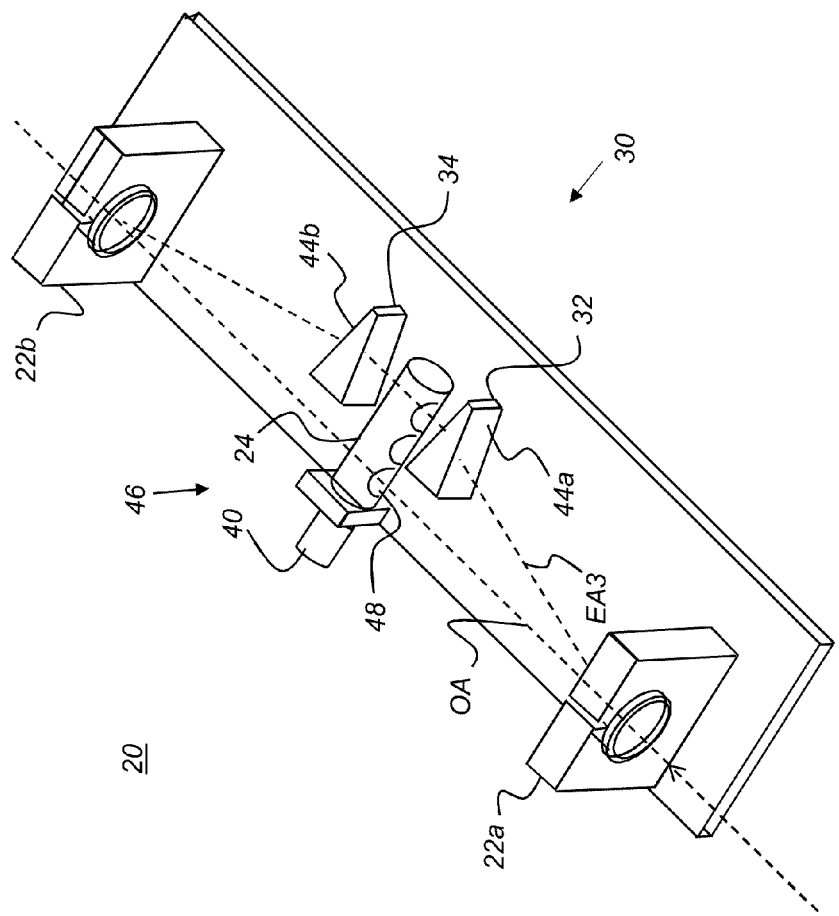
FIG. 6A is a perspective view that shows a broadband polarization switching apparatus using a pair of redirecting prisms in the path of the deviated polarization state.
Figure 6B:
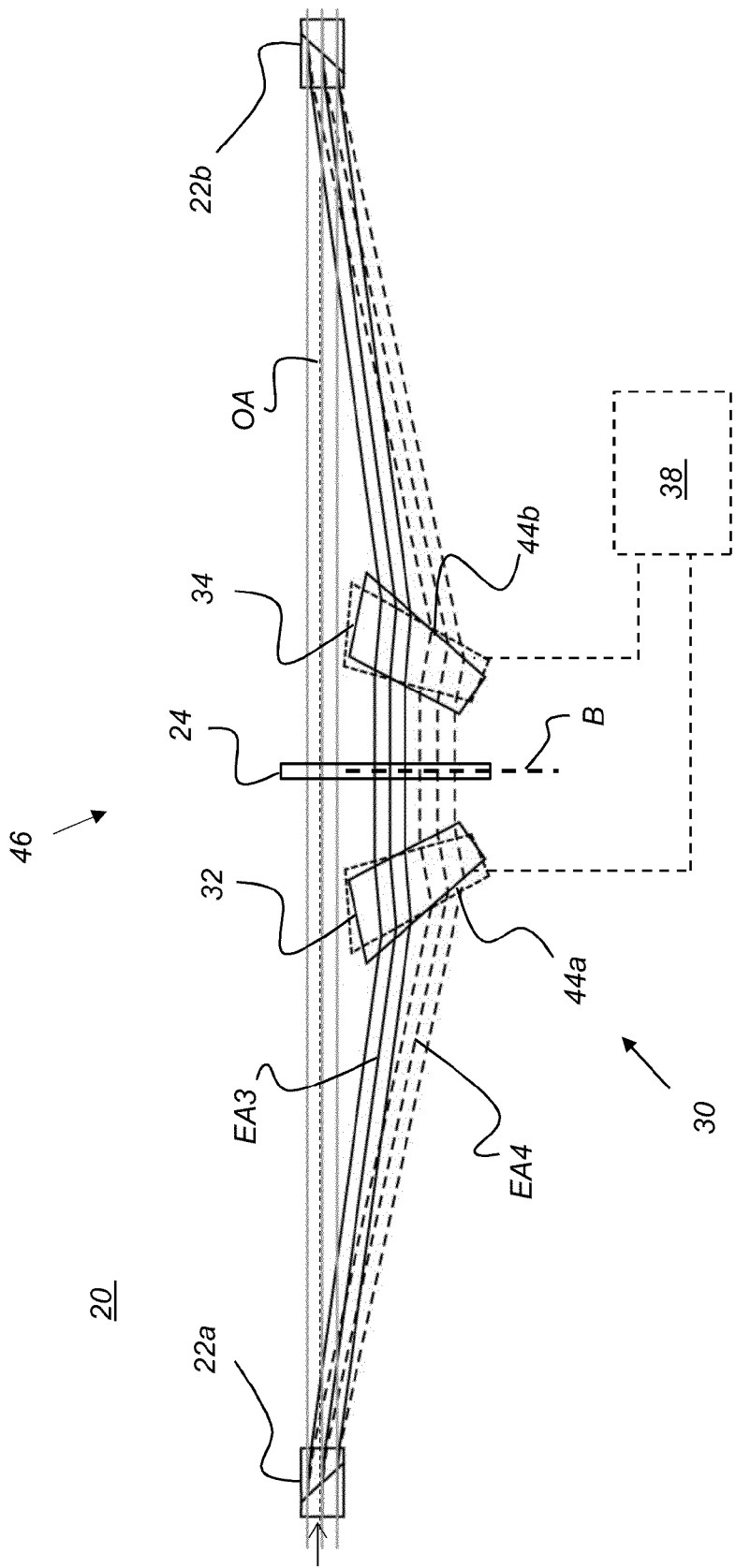
FIG. 6B is a schematic diagram for the apparatus shown in FIG. 6A.

The perspective view of FIG. 6A and schematic view of FIG. 6B show an alternate embodiment of the present invention that surmounts this difficulty and provides a way to adapt to the angle of minimum deviation $\delta_m$. Here, redirecting optics 30 utilize two refractive prisms 32 and 34 for redirecting light toward polarizer 22b. These prism components are symmetrically pivoted to actively accommodate wavelength-dependent alignment characteristics. With this arrangement, paired prisms 32 and 34 effectively act as a single prism, adjustable to satisfy the angular conditions for minimum deviation at a given wavelength. The angle of light at incidence face 44a is the same as the angle of exiting light at exit face 44b. Symmetry is about a plane of bisymmetry B, orthogonal to the page of FIG. 6B. At minimum deviation, the light between prisms 32 and 34 is normal to the plane of bisymmetry B and, in embodiments of switching apparatus 20 shown herein, parallel to the optical axis OA. By comparison with FIG. 5B, light along different axes EA3 and EA4 from the first polarizer 22a can be directed to second polarizer 22b with proper adjustment of prism 32 and 34 angle.

In the example shown in FIG. 6B, the two prisms 32 and 34 are identical in shape and are rotated in equal but opposite directions when switching wavelengths. Prisms 32 and 34 are manually pivoted or pivoted automatically using optional actuator 38. The two prisms and their respective pivot points are symmetrically arranged, so that the pivot point of each prism 32 and 34 is the same distance from the nearest respective polarizer 22a or 22b and the same distance from the optical axis OA. It can be observed that other arrangements using two or more movable prisms to provide minimum deviation at different wavelengths are possible, including more complex configurations than those shown in FIG. 6B.

Shutter elements 24 in the FIGS. 5A and 6A embodiments have a rotated tube with apertures 48 that align with the light along axes OA and EA at various positions. Shutter element 24 can have a number of different positions and states, such as with one position for each polarization state individually, one for both polarization states, and another position for neither polarization state, blocking all light. It can be appreciated that any of a number of alternate types of shutter mechanism can be used with shutter elements 24 positioned at any suitable location along the light paths, before, after, or within redirecting optics 30.

Figure 7:
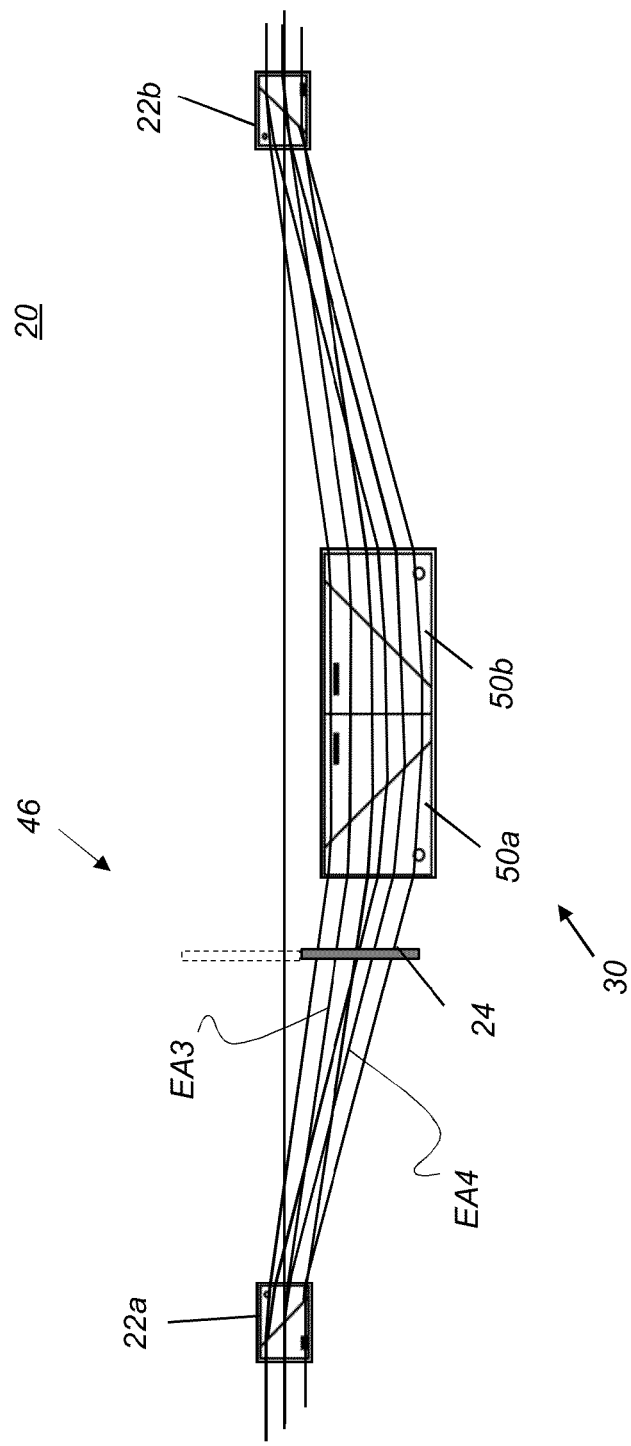
FIG. 7 is a schematic view that shows a broadband polarization switching apparatus using a second pair of polarizers in the path of the deviated light of the second polarization state.

The schematic view of FIG. 7 shows an alternate embodiment of the present invention in which redirecting optics 30 use third and fourth composite birefringent polarizers 50a and 50b to redirect the light of the second polarization state back toward second polarizer 22b. Birefringent polarizers 50a and 50b, such as Rochon polarizers, are disposed in reversed orientation relative to each other, as described previously with reference to the first and second polarizers 22a and 22b. The arrangement of FIG. 7 helps to accommodate chromatic dependencies for light of the second polarization state, including variability in the EA angle due to wavelength. Unlike the embodiment shown in FIGS. 6A and 6B, the FIG.

7 embodiment does not require movement of any of the redirecting optics 30 components for a change in wavelength. As shown in FIG. 7, for example, light along both axes EA3 and EA4 is accommodated, as well as light at angles between those of axes EA3 and EA4.

The Rochon polarizer is advantaged for its broad spectral range, including the capability for handling light in the deep ultraviolet (DUV) region, such as around 200 nm. It should be observed that other types of birefringent polarizers could alternately be used, over appropriate wavelength ranges and power levels. Composite prism solutions such as the Wollaston, Senarmont, or Glan-Foucalt prisms could alternately be used for input and output polarizers 22a and 22b, for example, or for polarizers 50a and 50b used in redirecting optics, as was shown in FIG. 7, with appropriate redirection optics for the different polarization states.

Figure 8:
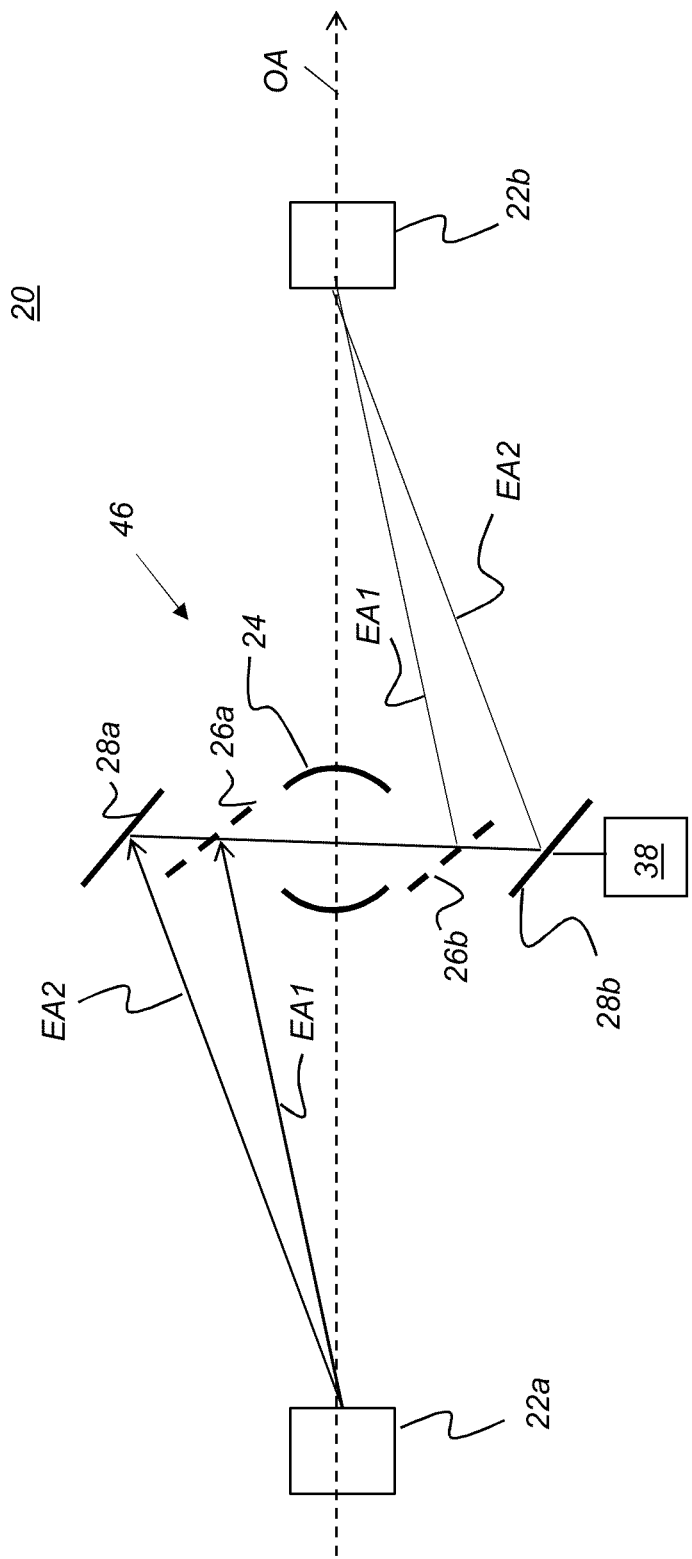
FIG. 8 is a schematic view that shows an alternate embodiment with paired reflectors folding the light path.

Consistent with an embodiment of the present invention, another type of adjustment for wavelength relates to reflector angle. FIG. 8 is a schematic view that shows an alternate embodiment of apparatus 20 with paired reflective elements folding the light path of the extraordinary axis for light of the second polarization, according to wavelength. Actuator 38 adjusts the reflective element angles and positions needed for redirecting light of different wavelengths to the second polarizer 22b.

At shorter wavelengths, axis EA2 is folded by paired reflectors at alternate positions shown for reflective elements 28a and 28b. At longer wavelengths, axis EA1 is folded by paired reflectors at positions shown for reflective elements 26a and 26b. These may be the same pair of reflectors at different positions or may be reflectors that are provided in fixed positions for particular wavelengths. For the first undeviated polarization state that is orthogonal to the polarization state of light along EA1 or EA2, all wavelengths are directed along optical axis OA. It should be noted that reflective elements at positions shown for elements 28a and 26a can be interpreted as alternative positions of the same mirror or other movable reflective surface. According to an embodiment of the present invention, a single mirror is translated to a position that is suitable for the wavelength of incident light. For relatively shorter wavelengths, the mirror is positioned at or nearer the position shown for reflective element 28a. For relatively longer wavelengths, the mirror is positioned at or nearer the reflector positioned at reflective element 26a. The paired mirror is symmetrically placed in appropriate positions as reflective elements 26b and 28b. Depending on the application, mirrors can be automatically actuated to translate and rotate to the appropriate position and angle. Alternately, manual mirror adjustment can be used.

Embodiments of the present invention can be packaged as part of a measurement apparatus, for example, allowing automated measurement of surface or physical characteristics using light over a range of wavelengths and with or without concern for polarization state. Advantageously, the polarization switching apparatus of the present invention handles light over a broad range of wavelengths, allows fast switching and reconfiguration, and allows light of either polarization or, alternately, all incident light to be projected toward a target. Alternately, all incident light can be blocked as needed. In this way, a four-state shutter apparatus 46 can be provided, so that polarization switching apparatus 20 allows light of a first polarization state, light of a second polarization state, light of all polarization states, or no light to be provided at the output.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. A polarization switching apparatus comprising:
   a first birefringent polarizer formed as a composite prism and disposed to direct incident light of a first polarization along a first optical path and light of a second polarization along a second optical path, wherein the second optical path is oblique with respect to the first optical path;
   a beam redirector disposed to redirect the first optical path from the first birefringent polarizer toward an input face of a second birefringent polarizer; wherein the second birefringent polarizer is also formed as a composite prism and is disposed to combine incident light of the first and second polarizations onto a common output path; and
   a shutter apparatus that is actuable to selectively block light of the first polarization or light of the second polarization from the input face of the second birefringent polarizer.

2. The polarization switching apparatus of claim 1 wherein at least the first birefringent polarizer is a Rochon polarizer.

3. The polarization switching apparatus of claim 1 wherein the first birefringent polarizer comprises component prisms formed from one or more of calcite, quartz, $MgF_2$, $YVO_4$, or alpha-BBO (barium borate).

4. The polarization switching apparatus of claim 1 wherein the shutter apparatus is further actuable to selectively block light of both first and second polarizations.

5. The polarization switching apparatus of claim 1 wherein the beam redirector comprises at least one reflective element.

6. The polarization switching apparatus of claim 1 wherein the beam redirector comprises a third polarizer and a fourth polarizer.

7. The apparatus of claim 1 wherein the beam redirector comprises at least one prism.

8. The polarization switching apparatus of claim 1 wherein the shutter apparatus has an actuator taken from the group consisting of a galvanometric actuator and a motor.

9. The apparatus of claim 1 wherein the first and second polarizers comprise crystalline materials and provide polarization of light having wavelengths in the ultraviolet region from about 200 nm to 250 nm.

10. The apparatus of claim 1 wherein the beam redirector comprises two prisms that are each movable to adjust for angle of minimum deviation.

11. A polarization switching apparatus comprising:
    a first birefringent polarizer and a second birefringent polarizer, each formed as a composite prism with an input face and an output face, and both disposed on an optical axis, wherein the second birefringent polarizer has a reversed orientation from the first birefringent polarizer;
    a beam redirector disposed to redirect obliquely directed light of a first polarization from the output face of the first birefringent polarizer toward the input face of the second birefringent polarizer; and
    a shutter apparatus actuable to selectively block either light along the optical axis between the first and second birefringent polarizers or the light of the first polarization, and to pass light of one polarization toward the second birefringent polarizer and block light of another polarization.

12. The polarization switching apparatus of claim 11 wherein at least the first birefringent polarizer is a Rochon polarizer.

13. The polarization switching apparatus of claim 11 wherein the beam redirector comprises at least one reflective element.

14. The polarization switching apparatus of claim 11 wherein the beam redirector comprises a third birefringent polarizer and a fourth birefringent polarizer.

15. The apparatus of claim 11 wherein the beam redirector comprises at least one prism.

16. The apparatus of claim 11 wherein the first and second birefringent polarizers are composite prisms formed from two coupled prisms of crystalline materials.

17. The apparatus of claim 11 wherein the beam redirector comprises an actuator for redirecting light at two or more different angles.

18. The polarization switching apparatus of claim 11 wherein the shutter apparatus has an actuator taken from the group consisting of a galvanometric actuator and a motor.

19. A method for switching polarization of incident light, the method comprising:

disposing a first birefringent polarizer and a second birefringent polarizer on an optical axis, wherein both first and second birefringent polarizers are composite prisms, each having an input face and an output face, wherein the second birefringent polarizer has a reversed orientation from the first birefringent polarizer;

disposing a beam redirector in the path of obliquely directed light from the first birefringent polarizer to redirect the obliquely directed light toward the second birefringent polarizer;

directing incident light along the optical axis and toward the input face of the first birefringent polarizer; and actuating a shutter apparatus to selectively block at least the obliquely directed light from the first birefringent polarizer, thereby passing light of one polarisation toward the second birefringent polarizer, and blocking light from another polarization.

20. The method according to claim 19 further comprising actuating the shutter apparatus to selectively block light along the optical axis between the first and second birefringent polarizers.

* * * * *